(12) United States Patent
Patron

(10) Patent No.: US 7,041,073 B1
(45) Date of Patent: May 9, 2006

(54) CUSTOM FIT CERVICAL COLLAR

(76) Inventor: Martin Rizo Patron, 766 Cypress Walk, Apt. E, Santa Barbara, CA (US) 93117

( * ) Notice: Subject to any disclaimer, the term of this patent is extended or adjusted under 35 U.S.C. 154(b) by 0 days.

(21) Appl. No.: 11/120,247

(22) Filed: May 2, 2005

(51) Int. Cl.
*A61F 5/00* (2006.01)
(52) U.S. Cl. ............................. 602/17; 602/18; 602/19
(58) Field of Classification Search ............ 602/17–19; 128/DIG. 23
See application file for complete search history.

(56) References Cited

U.S. PATENT DOCUMENTS

| | | | | |
|---|---|---|---|---|
| 4,413,619 A | * | 11/1983 | Garth | 602/18 |
| 5,058,572 A | * | 10/1991 | Schmid et al. | 602/18 |
| 5,215,517 A | * | 6/1993 | Stevenson et al. | 602/18 |
| 5,593,382 A | * | 1/1997 | Rudy et al. | 602/18 |
| 5,865,773 A | * | 2/1999 | Koledin | 602/18 |
| 6,921,376 B1 | * | 7/2005 | Tweardy et al. | 602/18 |

* cited by examiner

*Primary Examiner*—Henry Bennett
*Assistant Examiner*—Dinnatia Doster Greene
(74) *Attorney, Agent, or Firm*—Andrew Y. Schneder

(57) ABSTRACT

A cervical collar comprising an inner and an outer region, a spinal support region, an occipital support region and a neck support region, said spinal support region including upper edges, lower edges, and side edges, a fastening strap affixed to said upper edge of spinal support region, a bridge member connecting occipital support region with spinal support region, said bridge member adapted to fold with a hinging means, said occipital support region including an upper edge, lower edges, a side edge, and anchoring strap affixed to said side edge, said neck support region including an upper edge, a side edge, and a sternum edge, said upper edge affixed with cooperating hooks, a dual adjustment system located on neck support region including tabs, female members, locking teeth, windows and bars, said tab affixed with said pawl, said pawl to engageably fit said locking teeth, said inner region comprising foam adhesively affixed to plastic, said inner region including a mandible support on neck support region, said mandible support adaptable to fold inwardly and outwardly by a hinging means.

9 Claims, 5 Drawing Sheets

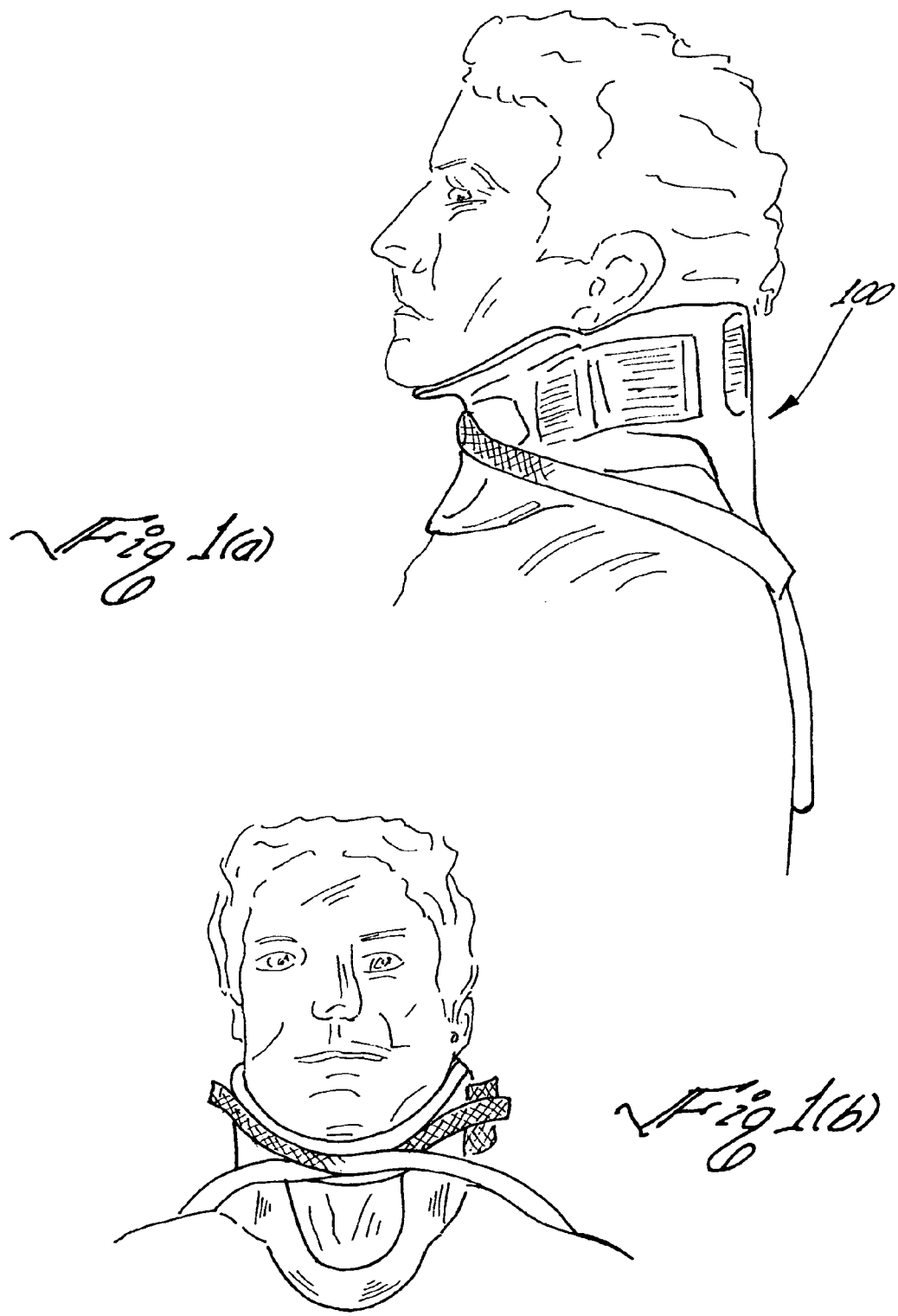

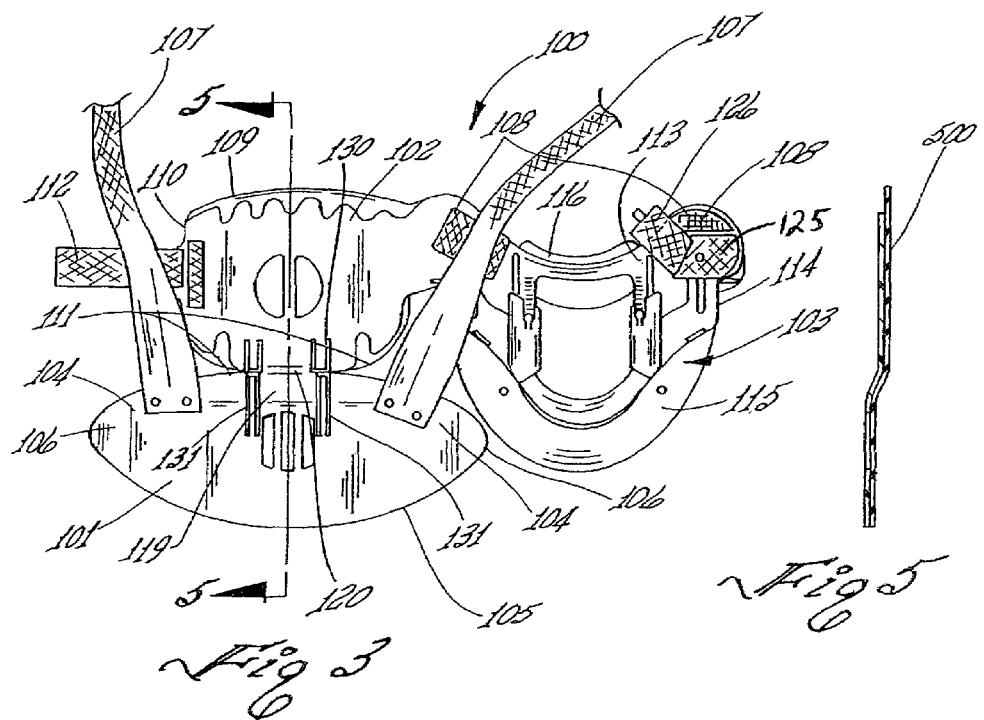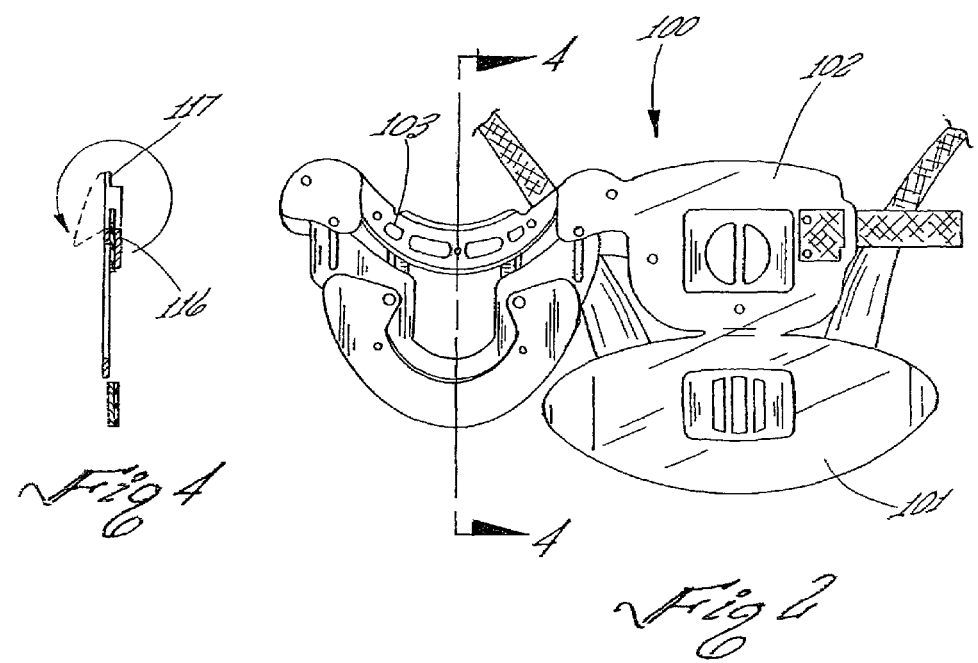

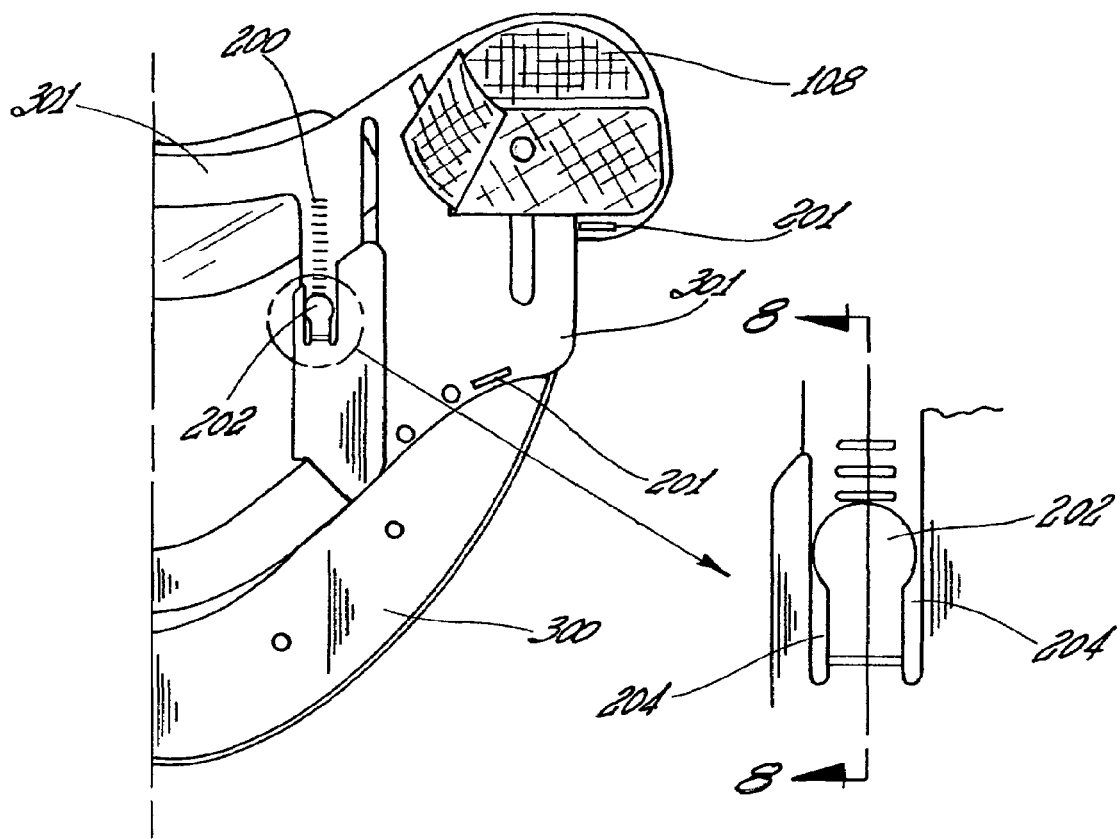
Fig 6
Fig 10
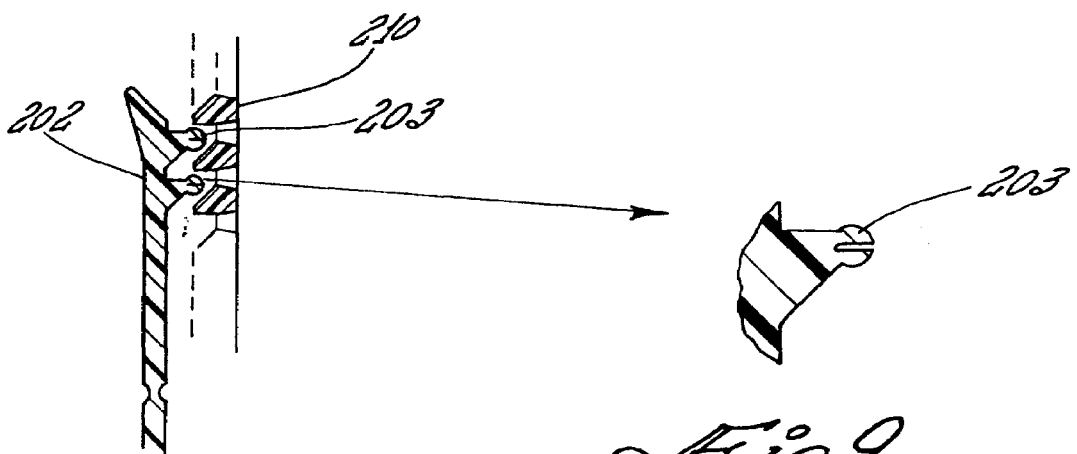
Fig 8
Fig 9

CUSTOM FIT CERVICAL COLLAR

FIELD OF THE INVENTION

The present invention is in the area of cervical collars, and more particularly an improved cervical collar, which substantially immobilizes the head and neck regions of a person in relation to the thorax.

BACKGROUND OF THE INVENTION

As per standard emergency protocols, first responders such as firefighters and paramedics must allocate at least one person to initiate cervical spine immobilization protocol with a trauma or accident victim with suspected head, neck or spinal injuries. The reason for this is in part to immobilize the victim's head to prevent or at least mitigate further injury to the neck region and/or spinal column. If a trauma or accident victim moves their neck or head in any direction, serious and debilitating injuries may ensue.

Currently, the marketplace does not offer a cervical collar which sufficiently immobilizes the head, neck and spinal regions of a victim. In fact, if one were to put on a standard cervical collar, one would find that there is very little restriction as to the movement of one's head and neck regions in relation to thorax. These cervical collars are not enabled with sufficient impediments to adequately immobilize victim's head.

This deficiency is manifested most fully when an accident victim is to be transferred on to a backboard. A standard cervical collar will simply not sufficiently restrict movement of neck regions in relation to the thorax so that an aid rescuer may move the victim in a safer way. And because standard cervical collars do not restrict movement, one first responder is incapable of initiating spinal stabilization upon a multiple number of victims.

While there are cervical collars on the market that do offer some support for trauma victims they do not completely immobilize victim. In fact, a person fitted with a standard cervical collar can move their head up, down, and sideways with significant degrees of range. In addition, the neck region will move in respect to the thoracic cavity and may exacerbate existing injuries.

Another troublesome deficiency of today's cervical collars is that there is no way to safely adjust the neck size of victim's collar after the cervical collar is placed on victim. Currently, an aid rescuer must make a rough estimate as to which size a victim's neck is and hope his guess reasonably approximates victim's neck size in order to adjust the neck brace before putting on patient. If rescuer's guess is not close, rescuer either must take off the cervical collar or leave the cervical collar on and hope that injuries to victim is not thereby exacerbated. Moreover, oftentimes, in the heat of the moment in an emergency an aid rescuer does not have enough time to properly size up victim's neck.

Therefore, what is clearly needed in the art is an improved cervical collar that will better immobilize a victim's head, neck, and thoracic regions. In addition, it is necessary to develop a cervical collar which offers substantial support to said regions. Furthermore, the emergency medical field is in need of a cervical collar that is designed to be custom fitted to the patient's physique after it is placed on the patient's neck. The market place does not offer a device with such capabilities which is also especially designed for extrication and rescue operations

SUMMARY OF THE INVENTION

A cervical collar comprising an inner and an outer region, a spinal support region, an occipital support region and a neck support region, said spinal support region including upper edges, lower edges, and side edges, a fastening strap affixed to said spinal support region, a bridge member connecting occipital support region with spinal support region, said bridge member adapted to fold with a hinging means, said occipital support region including an upper edge, lower edges, a side edge, and anchoring strap affixed to said side edge, said neck support region including an upper edge, a side edge, and a sternum edge, said neck support region also comprising a free layer and a stationary layer, free and stationary layers affixed via fastening means, said upper edge affixed with cooperating hooks, a dual adjustment system located on neck support region including locking tabs, locking teeth, adjusting tabs, said locking tab housed within a window, said inner region comprising foam adhesively affixed to plastic, said inner region including a mandible support on neck support region, said mandible support adaptable to fold inwardly and outwardly by a hinging means.

In some preferred embodiments, the cervical collar is made of plastic. In some preferred embodiments the cervical collar has a cooperating hook on neck support region is and comprised of an adhesively fixed layer and a free layer for engaging anchoring strap of occipital support region. In some preferred embodiments, the cervical collar has locking teeth which are substantially shaped as right triangles. In some preferred embodiments, the cervical collar has a sternum edge of neck support region is sized to protrude to cover the clavicles of a human being.

In some preferred embodiments, the cervical collar has a bridge member which is ergonomically designed to approximate the natural curvature of a human spine. In some preferred embodiments, the cervical collar has an anchoring strap which is enabled by cooperating hooks and loops material.

In some preferred embodiments, the cervical collar has fastening straps which are enabled by cooperating hooks and loops material. In some preferred embodiments, the cervical collar has a cooperating hook of free layer and fixed layer are enabled by cooperating loops and hooks material.

A method for placing cervical collar of claim one on a person comprising the steps of:
 (a) Unfolding mandible support and unfolding spinal support region
 (b) wrapping cervical collar around a person with mandible support placed toward person's chin;
 (c) fastening anchoring strap of occipital support region with fixed layer of claim 3
 (d) overlaying free layer with anchoring strap
 (e) simultaneously pressing tabs downwardly and pulling tabs downwardly or upwardly to adjust neck size
 (f) releasing tab when correct neck size is reached and locking the device by pressing the locking tabs.
 (g) wrapping fastening strap over person's shoulder and affixing with corresponding cooperating hook In some preferred embodiments, the method incorporates an outer region of extrication collar which is made of plastic. In some preferred embodiments, the method incorporates a cooperating hook on neck support region which is comprised of an adhesively fixed layer and a free layer for engaging anchoring strap of occipital support region. In some preferred embodiments, the method incorporates locking teeth which are substantially shaped as right triangles. In some preferred embodiments, the method incorporates a sternum edge of neck support region which is sized to protrude beyond the clavicles of a human being. In some preferred embodiments, the method incorporates a bridge member which is ergonomically designed to approximate the natural curvature of a human spine. In some preferred embodiments, the method incorporates an anchoring strap which is enabled by both loops material and hooks material. In some preferred embodiments, the method incorporates fastening straps which are enabled by loops material and hooks material. In some preferred embodiments, the method incorporates a cooperating hook of free layer and fixed layer are enabled by loops material and hooks material. In some preferred embodiments, the method further comprises the additional step of unfolding extrication collar before placing on person. In some preferred embodiments, the method further comprises the additional step of disengaging extrication collar from person by disengaging fastening straps and anchor straps from corresponding hooks.

BRIEF DESCRIPTION OF THE DRAWING FIGURES

FIG. 1a is a perspective view of a preferred embodiment of the present invention.

FIG. 1b is a perspective view of a preferred embodiment of the present invention.

FIG. 2 is a perspective view of a preferred embodiment of the present invention.

FIG. 3 is a perspective view of a preferred embodiment of the present invention.

FIG. 4 is a plan view of a preferred embodiment of the present invention.

FIG. 5 is a plan view of a preferred embodiment of the present invention.

FIG. 6 is a plan view of a preferred embodiment of the present invention.

FIG. 8 is a cross-sectional view of a preferred embodiment of the present invention.

FIG. 9 is a plan view of a preferred embodiment of the present invention.

FIG. 10 is a plan view of a preferred embodiment of the present invention.

DESCRIPTION OF PREFERRED EMBODIMENTS

Figure 7:
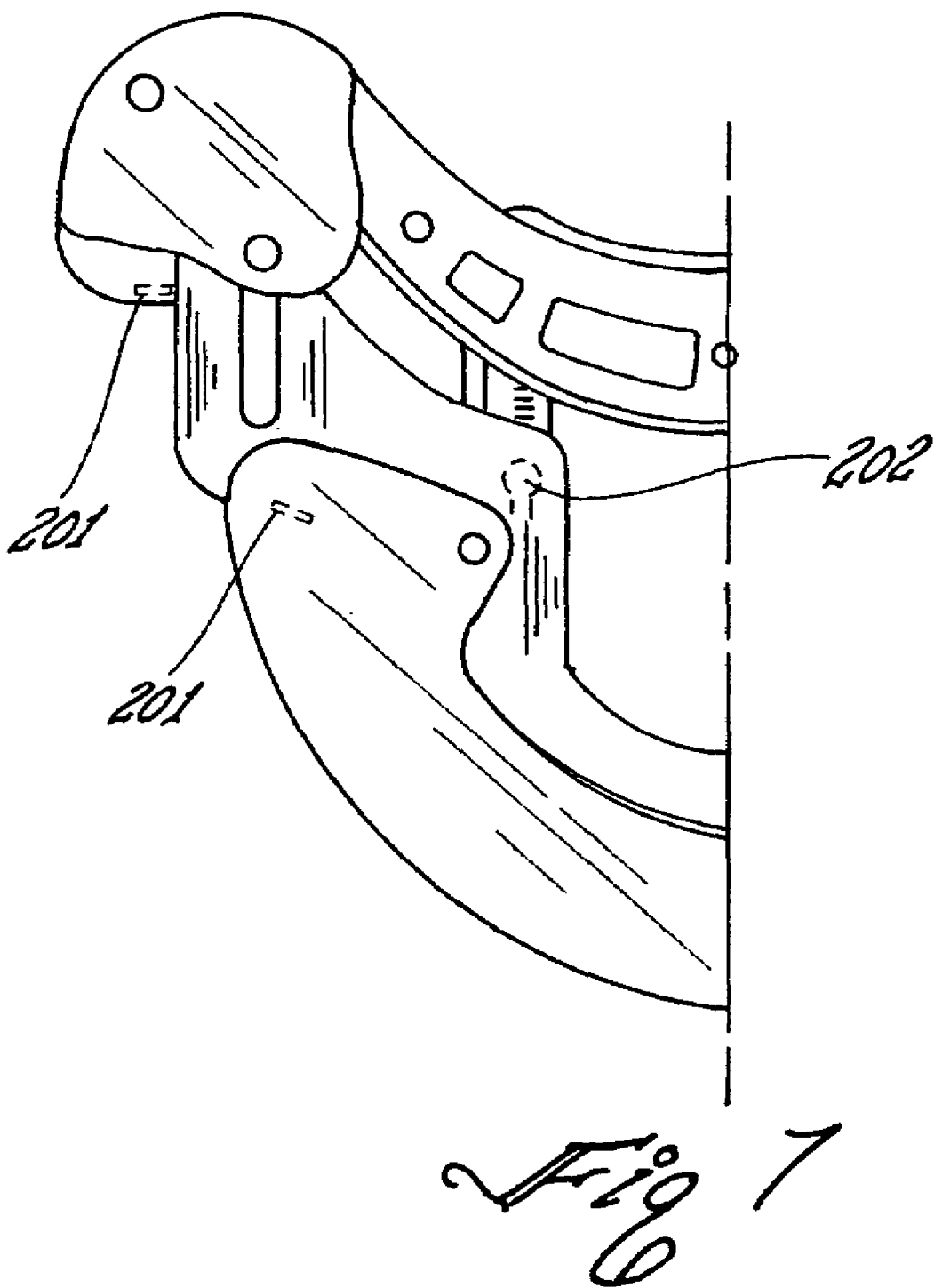
FIG. 7 is a plan view of a preferred embodiment of the present invention.

According to a preferred embodiment of the present invention, an article of manufacture is used for the immobilization of the cervical region of an injury victim by rescuers. The article of manufacture and accompanying method will be explained in enabling detail below.

FIGS. 1a and 1b are perspective views of a preferred embodiment of the present invention. Cervical collar 100 is made of a flexible plastic sheet material or injected plastic material. However, other materials may also be used to compose the cervical collar 100. As such, the use of plastic is not specifically required in the present invention.

FIG. 2 is a perspective view of a preferred embodiment of the present invention. The present invention can be described as having three discernable regions. The preferred embodiment includes a spinal support region 101, an occipital support region 102 and a neck support region 103. (Notwithstanding the fact there are three discernable regions, it is understood that the present invention is not necessarily an assemblage of three different parts). The circumferential length of cervical collar 100 measured from the far side of occipital support region 102 and far side of neck support region 103 has sufficient length to encircle a victim's neck. Cervical collar 100 may be manufactured in several different sizes to accommodate various sizes of different people.

Spinal support 101 is located below occipital support region 102. Located transversely from occipital support region 102 is the neck support region 103. In addition, for purposes of clarification, "outer region" shall hereinafter refer to the side that faces outside. And "inner region" shall hereinafter refer to the side that comes into contact with victim's skin. FIG. 5 shows a cross-section view of inner region which is adhesively layered with a foam material 500 for patient's comfort.

FIG. 3 is an isometric view of a preferred embodiment of the present invention. Turning now to the spinal support region 101, the spinal support region 101 includes upper edges' 104, lower edge' 105, and side edges' 106. The spinal support region functions as an anchoring point for the fastening straps 107. Affixed to spinal support 101 are the fastening straps' 107. The inside and outside faces of fastening straps' 107 are enabled by VELCRO® (a trademarked material). These faces comprise both hooks material and inner loops material for the purpose of being detachably secured to each other. Fastening straps' 107 are used to conjoin with cooperating hook 108. Cooperating hooks 108 are located on neck support region 103.

Fastening straps' 107 are long enough to wrap around the neck and over the shoulder of the victim to clasp onto cooperating hook 108 situated on both sides upon the upper portion of the neck support region 103. Fastening straps 107 are used to create an interference fit of cervical collar 100 in relation to head, neck and thorax regions of body Connecting spinal support region 101 and occipital support region 102 with occipital support region is the bridge member 119. Bridge member 119 is ergonomically designed to approximate the natural curve of the human spine. This ergonomic design allows for a better fit and will help mitigate further injury to victim. In addition, bridge member 119 is enabled to fold via hinging means 120.

Also, Bridge member 119 is specifically designed to prevent over-extension between occipital support 102 region and spinal support region 101. Bridge member 119 has occipital support members 130 and spinal support members 131. Occipital support members 130 have an added barrier which forms perpendicularly at a right angle. This added barrier comes into direct contact with spinal support member 131. The contact between the barrier of occipital support member 130 and spinal support member 131 prevents overextension between spinal support region 101 and occipital support region 102.

Situated directly above spinal support region 101 is occipital support region 102. Occipital support region 102 comprises upper edge "109, side edge "110 and lower edges "111. Affixed to side edge 110 is a Velcro® enabled anchoring strap "112. Anchoring strap "112 is made to conjoin with cooperating hook" 108 located on neck support region 103.

Turning now to the neck support region 103, the neck support region 103 comprises an upper edge "'113, a side edge'" 114, and a sternum edge'" 115. Situated on opposite sides of upper edge "'113 are two cooperating hooks 108. And situated on inside of neck support region is the mandible support 116.

FIG. 4 is an isometric view of the mandible support 116 is affixed to upper edge 113 via a hinging means 117. There are two hinging means located on both sides of mandible support 116. Sternum edge "'115 is elongated and is of sufficient length as to cover the clavicles of a victim.

Referring back now to FIG. 3, situated near side edge 114 is cooperating hook 108. Cooperating hook "108 is dual layered into a Fixed Layer 125 and Free Layer 126 (also called 108). Fixed layer (also known as cooperating hook 108) is adhesively affixed to the plastic. And the Free Layer 126 is connected continuously with the Cooperating hook 108. Free Layer 126 is used to provide an additional means of support. After fastening strap 107 is placed upon Cooperating hook 108, Free Layer 126 is placed upon anchoring strap strap 112.

In addition, neck support region 103 comprises a free layer 300 and a stationary layer 301. More details are discussed below.

FIGS. 6 and 7 illustrate a dual tab self-locking adjustment system 200 (hereafter DAS 200). DAS 200 is located on opposite sides of neck support region 103. DAS 200 is made for adjusting the length between bottom of sternum edge 115 and upper edge "'113. The unique design of the DAS 200 allows the rescuer to custom-fit the neck cervical collar 100 to brace the patient's physique once the cervical collar 100 has been placed upon the patient's neck. This ensures the best fit and provides for better immobilization.

In order for DAS 200 to operate, there must be two layers on the neck support region 103. Free layer 300 is situated under stationary layer. Free layer 300 comprises the sternum edge 115. Free layer 300 is fastened to stationary layer 301 by fastening means. In a preferred embodiment, fastening means may be rivets.

DAS 200 comprises adjusting tabs 201 (shown in FIG. 10), locking tabs 202, locking teeth 203 (shown in FIG. 8 and FIG. 9) female members 210, and windows 204 (see FIG. 10). Locking teeth 203 are made to engageably fit with female members 210. Locking tab 202 is connected with locking teeth 203 which directly engages with female members 210.

In order to operate DAS 200, a person places fingers on all four adjusting tabs 201. Thereafter, DAS 200 is adjusted by moving free layer 300 by exerting pressure on adjusting tabs 201 in opposite directions. After free layer 300 is moved sufficiently far enough to fit victim's neck size, DAS 200 is locked via locking tabs 202 and locking teeth 203. After positioning is finished, a person simply pushes on both locking tabs 202 simultaneously to engage and lock with locking teeth 203.

Figure 11:
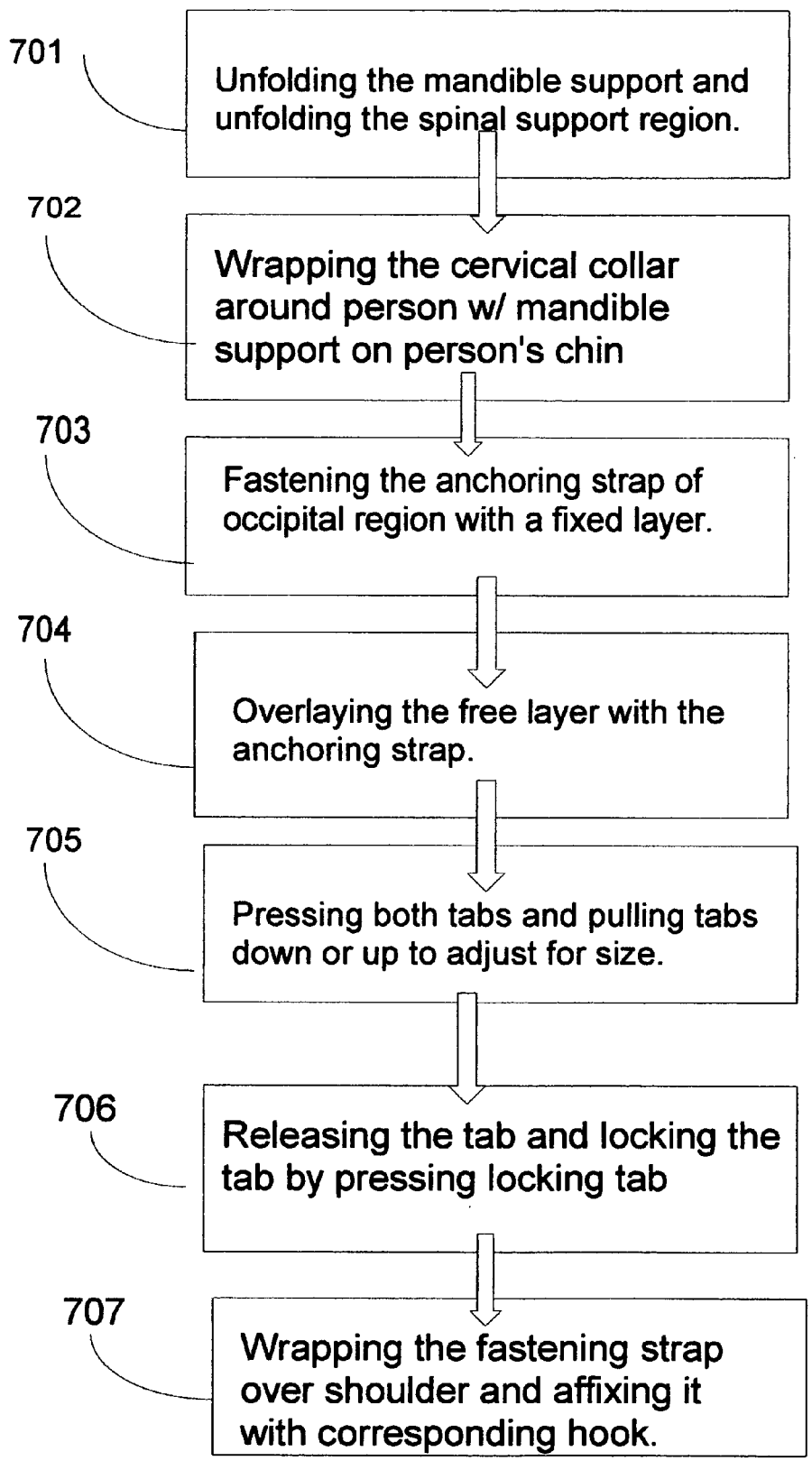
FIG. 11 is a flow diagram of a preferred method of the present invention.

FIG. 11 is a flow diagram of the method of the present invention. The method of the present invention includes the following steps: 701 unfolding the mandible support and unfolding the spinal support region, 702 wrapping the cervical collar around a person with the mandible support placed toward the person's chin, 703 fastening the anchoring strap of occipital region with a fixed layer, 704 overlaying the free layer with anchoring strap, 705 simultaneously pressing tabs downwardly and pulling tabs downwardly or upwardly to adjust the neck size, 706 releasing the tab when the correct neck size is reached and locking the device by pressing the locking tabs, and 707 wrapping the fastening strap over a person's shoulder and affixing it with the corresponding hook.

It will be apparent to the skilled artisan that there are numerous changes that may be made in embodiments described herein without departing from the spirit and scope of the invention. Other features not mentioned in the specification, but known to one skilled in the art may be integrated as well without departing from the spirit and scope of the present invention. There are, for example, a wide array of materials, apparatuses, and methods which may be interchangeably used there are many changes that may be made in dimensions and so forth to accommodate different needs which may be used, all within the scope of the invention. The methods, system, and apparatuses of the present invention should therefore be afforded the broadest possible scope under examination. As such, the invention taught herein by specific examples is limited only by the scope of the claims that follow.

What is claimed is:

1. A cervical collar comprising:
   an inner and an outer region, a spinal support region, an occipital support region and a neck support region,
   said spinal support region including upper edges, lower edges, and side edges, fastening straps affixed to said spinal support region,
   an ergonomically designed bridge member shaped to approximate the natural curve of a human spine connecting occipital support region with spinal support region,
   said bridge member adapted to fold with a hinging means, said bridge member is also designed to prevent over-extension between said occipital support region and said spinal support region with occipital support members and spinal support members,
   said occipital support region including an upper edge, lower edges, a side edge, and anchoring strap affixed to said side edge,
   said neck support region including an upper edge, a side edge, and a sternum edge, said neck support region also comprising a free layer and a stationary layer, free and stationary layers affixed via fastening means, said upper edge affixed with cooperating hooks, said free layer providing an extra layer of support with the attachment of anchoring strap and stationary layer, said anchoring strap used to connect said occipital support region with said neck support region by hooking anchoring strap to the stationary layer, and said free layer is hooked to said anchoring strap by over-laying free layer over said anchoring strap;
   a dual adjustment system located on neck support region including locking tabs, locking teeth, adjusting tabs and female members,
   said locking teeth to engageably fit with female members,
   said locking tab housed within a window and connected with said locking teeth,
   said inner region comprising foam adhesively affixed to plastic, said inner region including a mandible support on neck support region, said mandible support adaptable to fold inwardly and outwardly by a hinging means.

2. The cervical collar of claim 1 wherein outer region of extrication collar is made of plastic.

3. The cervical collar of claim 1 wherein cooperating hook on neck support region is comprised of an adhesively fixed layer and a free layer for engaging anchoring strap of occipital support region.

4. The cervical collar of claim 1 wherein locking teeth are substantially shaped as right triangles.

5. The cervical collar of claim 1 wherein sternum edge of neck support region is sized to protrude to cover the clavicles of a human being.

6. The cervical collar of claim 1 wherein bridge member is ergonomically designed to approximate the natural curvature of a human spine.

7. The cervical collar of claim 1 wherein anchoring strap is enabled by cooperating hooks.

8. The cervical collar of claim 1 wherein fastening straps are enabled by cooperating hooks and loops material.

9. The cervical collar of claim 3 wherein cooperating hook of free layer and fixed layer are enabled by cooperating loops and hooks material.

* * * * *